United States Patent [19]

Cordon

[11] Patent Number: 4,828,833

[45] Date of Patent: May 9, 1989

[54] DENTIFRICE HAVING DECREASED ABRASIVITY

[75] Inventor: Martin Cordon, Highland Park, N.J.

[73] Assignee: Colgate-Palmolive Company, New York, N.Y.

[21] Appl. No.: 130,142

[22] Filed: Dec. 8, 1987

[51] Int. Cl.$^4$ .............................................. A61K 7/22
[52] U.S. Cl. ........................................ 424/54; 424/49; 424/58
[58] Field of Search ............................. 424/49, 58, 54

[56] References Cited

U.S. PATENT DOCUMENTS

| | | | |
|---|---|---|---|
| 4,144,322 | 3/1979 | Cordon | 424/49 |
| 4,152,420 | 5/1979 | Gaffar | 424/49 |
| 4,282,204 | 8/1981 | Phillips | 424/49 |
| 4,627,977 | 12/1986 | Gaffar et al. | 424/52 |

*Primary Examiner*—Howard E. Schain
*Assistant Examiner*—F. T. Moezie
*Attorney, Agent, or Firm*—Robert L. Stone; Murray M. Grill

[57] ABSTRACT

Dentifrice compositions having decreased abrasivity and increased cleaning and stain removal properties comprising an abrasive system and about 0.1–2% of a linear high molecular weight polymer selected from the group consisting of polyacrylamide derivatives such as partially hydrolyzed polyacrylamide and double substituted guar gum derivatives such as hydroxypropylated carboxymethylated guar gum.

14 Claims, No Drawings

DENTIFRICE HAVING DECREASED ABRASIVITY

BACKGROUND OF THE INVENTION AND PRIOR ART

This invention relates to a dentifrice having reduced abrasivity and increased cleaning and stain removal properties comprising a linear water-soluble, polymer having a high molecular weight of over 1,000,000 selected from the group consisting of polyacrylamide derivatives such as partially hydrolyzed polyacrylamide, and guar gum double derivatives such as hydroxypropylated carboxymethylated guar gum, and an abrasive system of dentally acceptable polishing agents, typically selected from the group consisting of a siliceous polishing agent, a calcined alumina and mixtures thereof.

It has been difficult heretofore to provide dentifrices for use in the daily brushing and cleaning of teeth which provides a desirable balance of cleaning and abrasive action. This has been largely due to the difficulty in selecting suitable abrasives which will afford maximum removal of difficult stains and debris without damaging the oral hard tissues (enamel, dentin and cementum), particularly the dentin surfaces.

The prior art has addressed the problem of decreasing the abrasivity of dentifrices as disclosed in U.S. Pat. No. 4,102,992 wherein water-insoluble organic polymers such as the thermoplastic acrylics (polymethyl methacrylate and polyisobutyl methacrylate), cellulosics, polyamides, polyethylene, polystyrene and the vinyls, which are less abrasive than the calcium carbonate polishing agent, are added to the dentifrice composition.

U.S. Pat. No. 4,144,322 discloses the reduction of enamel abrasiveness in dentifrices comprising a dental abrasive system of hydrated siliceous abrasive and the hard abrasive calcined alumina, and about 1-5% by weight of a calcium, magnesium or sodium salt which effects a reduction in the radioactive enamel abrasion (REA) of the dentifrice.

U.S. Pat. No. 4,407,788 and British Pat. No. 2,100,983B disclose a siliceous polishing material and a small amount of a water soluble resinous poly(ethylene oxide) and maltitol humectant which improves stain removal without raising radioactive dentin abrasion (RDA).

However, there is no disclosure of the use of the high molecular weight, linear, water soluble polymers, particularly partially hydrolyzed polyacrylamides and the hydroxypropylated carboxymethylated guar gum to reduce dentin abrasivity of a dentifrice composition containing an abrasion system having maximum cleaning and stain removal properties without causing undue abrasion to the oral hard tissues, particularly the dentin layer.

The prior art also discloses guar gum as a thickening agent per se, or in combination with other components, such as abrasives in dentifrice compositions as shown in U.S. Pat. No. 3,723,408 wherein is disclosed the process for preparing the hydroxyalkyl ether derivative of polygalactomannan (guar gum), but does not disclose the use of guar gum derivative and particularly, not for a double substituted guar gum derivative in a dentifrice to reduce dentin abrasivity.

U.S. Pat. No. 4,122,162 discloses oral compositions for inhibiting plaque, containing as the gelling agent, a cellulose ether, guar gum or colloidal silica, and conventional abrasives such as the calcium phosphates, alkali metal metaphosphates, silicon dioxide, hydrated alumina oxides and aluminum silicates. However, there is no disclosure of the hydroxypropylated carboxymethylated guar gum. There is no mention of abrasivity or stain removal.

U.S. Pat. No. 4,081,526 also discloses an antiplaque composition containing suitable gelling agents including guar gum and conventional polishing agents such as calcium phosphate dibasic dihydrate, calcium carbonate, calcium pyrophosphate, aluminum hydroxide, silica, kaolin or alumina. There is no mention of abrasivity or stain removal.

U.S. Pat. No. 4,374,823 discloses a dental composition having proper viscosity flow rate and ribbon shape retention containing a gelling agent mixture of xanthan and guar gum, a sorbitol humectant and a suitable water insoluble polishing agent.

However, there is no disclosure in the prior art of dentifrice compositions containing linear, water soluble, high molecular weight polymers selected from the gro consisting of polyacrylamide, partially hydrolyzed polyacrylamide and hydroxypropylated carboxymethylated guar gum, and any suitable dental polishing agent, typically a siliceous abrasive and/or a hard abrasive such as calcined alumina, having reduced dentin abrasivity and increased cleaning and stain removal properties.

SUMMARY OF THE INVENTION

It has now been found that the addition of about 0.1 to 2% and preferably about 1% by weight of a water soluble, linear, very high molecular weight polymer having a molecular weight above 1,000,000, selected from the group consisting of polyacrylamide derivative and double substituted guar gum derivative such as partially hydrolyzed polyacrylamide and hydroxypropylated carboxymethylated guar gum, to an abrasive system comprising a dentally acceptable polishing agent such as hydrated alumina, calcium carbonate, calcium pyrophosphate, dicalcium phosphate dihydrate, a siliceous polishing agent, calcined alumina, and mixtures thereof, effects a substantial reduction in the dentin abrasivity and improved stain removal properties of the dentifrice. This is a particularly desirable feature when applied to an abrasive system containing the hard abrasive calcined alumina. Dentifrice formulations can now be made containing hard abrasive (heretofore relatively undesirable because of their tendency to damage tooth dentin) to give superior stain removal and cleaning without encountering the problem of excess dentin abrasion. An advantage of this invention over the prior art is the improvement of the cleaning to abrasivity ratio of many dentifrice systems. Another advantage is that it makes possible the use of abrasive systems which would be unduly abrasive in the absence of the high molecular weight polymers of present invention.

Accordingly, it is a primary object of the instant invention to provide a dentifrice composition having decreased dentin abrasivity and improved cleaning properties in the presence of a water soluble, high molecular weight (greater than 1,000,000) linear polymer selected from the group consisting of partially hydrolyzed polyacrylamide and an hydroxypropylated carboxymethylated guar gum.

Another object of the invention is to provide a dentifrice having superior cleaning and stain removal properties without increasing the dentin abrasivity thereof comprising small amounts of the water soluble, linear, very high molecular weight polyacrylamide derivative or guar gum derivative polymer, and an abrasive system comprising a dentally acceptable polishing agent or mixture of polishing agents.

Additional objects, advantages and novel features of the invention will be set forth in part in the description which follows, and in part will become apparent to those skilled in the art upon examination of the following specification or may be learned by practice of this invention.

To achieve the foregoing and other objects in accordance with the present invention, as embodied and broadly described herein, the dentifrice compositions of this invention having reduced abrasivity and improved cleaning properties comprises an abrasive system consisting of at least 15% of a dentally acceptable polishing agent, preferably a siliceous polishing agent per se or in combination with calcined alumina, and an effective amount of about 0.1-2.0% by weight of a water soluble high molecular weight of above one million, linear polymer selected from the group consisting of polyacrylamide derivative, and a doubly substituted guar gum derivative, to reduce the dentin abrasion of the dentifrice, in a dental vehicle.

More specifically, present invention relates to a dentifrice composition having reduced dentin abrasivity and increased stain removal properties comprising about 15% to 75% and preferably 15-50% by weight of an abrasive system consisting of one or more dentally acceptable polishing agents, and about 0.1-2% by weight of a water soluble linear polymer having a molecular weight of about one million to six million selected from the group consisting of a partially hydrolyzed (about 10-35%) polyacrylamide and a hydroxypropylated carboxymethylated guar gum, as the dentin abrasivity reducing agent, in a dental vehicle containing about 20-80% by weight of a liquid phase comprising water and/or humectant.

DETAILED DESCRIPTION OF THE INVENTION

In accordance with this invention, the abrasive systems of dentally acceptable polishing agents are commercially well known. Representative polishing agents include, for example, hydrated alumina, calcium carbonate, magnesium carbonate, calcium pyrophosphate, dicalcium phosphate dihydrate, tricalcium phosphate, calcined alumina, siliceous polishing agents, etc. and mixtures thereof. The typical abrasive system of dental polishing agents is selected from the group consisting of a siliceous polishing agent, a calcined alumina and mixtures thereof.

Calcined alumina is a hard abrasive with a mean particle diameter of about 1 to 15 microns and preferably 1 to 10 microns. Flaked calcined alumina is defined as flat flakes of alpha-alumina crystals, of disc- or plate-like configuration, said flakes having a mean (by weight) particle diameter of less than about 7 microns (e.g. about 2 to 7 microns). Viewed under a scanning electron microscope, the flat alumina particles have sharp edges indicating that they have been fractured perpendicular to their flat parallel faces. Generally, the thickness of the flakes are less than about $\frac{1}{3}$ (e.g. about $\frac{1}{5}$ to 1/10) of their diameters, and are in the range of about $\frac{1}{2}$ micron (or less) to about 2 microns (e.g. about 1 microns). The flat alpha-alumina crystals and a process for preparing them are described in U.S. Pat. No. 3,121,623. Another calcined alumina abrasive useful herein is defined in U.S. Pat. No. 4,060,599, the disclosure of which is incorporated herein by reference, as crystals of alpha-alumina ground to its ultimate particle form and having a mean ultimate particle size of about 1 to 2 microns.

A calcined alumina product provided as RC-152 DBM is very dense and highly stable. It has a mean particle size between about 1 to 2 microns, typically about 1.6 microns.

Crystalline alumina RC-152 DMB is ground from a coarser alumina commercially available as RC-152. RC-152 has a crystal particle size such that 98% of the particles pass through a 200 mesh screen and 25% pass through a 100 mesh screen.

The siliceous polishing agent is soft in comparison to the calcined alumina, and has been conventionally used in toothpaste and dental gels. A siliceous polishing agent particularly useful herein is an amorphous alkali metal or alkaline earth metal aluminosilicate having a refractive index of about 1.44-1.46, and containing at least about 70% siliceous abrasive, up to about 10% alumina, up to about 20% by weight of moisture and up to about 10% by weight of sodium oxide, the moisture content preferably being about 10-20% by weight, measured by loss at 1000° C. and the typical content of sodium oxide being about 5-10% by weight. But when little alumina is present in the aluminosilicate, e.g., about 1% or less, the material can be a silica with combined alumina.

The siliceous dental polishing agent may have a particle size of about 2 to 40 microns and may also be present in the form of relatively large agglomerates (of the individually particles) of such size as to be visible to the naked eye but easily reduced to the fine impalpable particle size upon being subject to toothbrushing in the mouth. Such agglomerates may be agglomerated with or without binding agent which may be water-soluble or water-insoluble.

For most purposes it is preferable that the siliceous dental abrasive have a particle size less than 20 microns to avoid any gritty feel. Other suitable siliceous polishing agents include amorphous precipitated silica and a porous amorphous silica anhydride having an average particle size of about 1-20 microns such as a dehydrated silica hydrogel (i.e. a xerogel). Examples of such amorphous silicic anhydride polishing agents are known as "Syloid" Silica (Grace, Davison Chemical Co.) and "Santocel 100" (Monsanto Co.).

The proportion of the polishing agent content in the dentifrice composition is generally in the range of about 15-75% and preferably about 15-50% by weight of the dentifrice. When a hard abrasive polishing agent such as calcined alumina is used, it is preferable to use an additional softer polishing agent such as a siliceous polishing agent. The content of said hard abrasive may generally be about 5 to 20% and preferably 8 to 15% by weight of the dentifrice, and the content of the additional siliceous polishing agent may be in the range of about 10 to 50% and preferably about 20 to 50% by weight of the dentifrice, provided the total abrasive content is within the range of 15-75% by weight.

The water soluble high molecular weight linear polymer used in present invention to reduce dentin abrasivity and improve stain removal of the dentifrice is selected from the group consisting of polyacrylamide derivatives such as a partially hydrolyzed polyacrylamide, and guar gum derivatives such as a hydroxypropylated carboxymethylated guar gum, said polymers having a very high molecular weight of greater than 1 million.

The polyacrylamide polymers are usually prepared by the free-radical polymerization of acrylamide in aqueous solution and sold as such or dried and sold as a powder. The very high molecular weight polymers are sold as a powder. Hydrolysis to the carboxylate ion converts the essentially neutral polyacrylamide to a strongly anionic molecule. Under alkaline conditions the hydrolysis progresses readily to about 35% particularly when the molecular weight of the polymer is about 1,000,000 to 5,000,000. When it is higher, (e.g. about 10,000,000 to 50,000,000) hydrolysis is typically about 10-15%. Superfloc 204, a commercial polyacrylamide derivative obtainable from American Cyanamide Co., is an anionic partially hydrolyzed (about 35% carboxyl) polyacrylamide with an average molecular weight in the area of 4 million. It is a white, free-flowing granular solid, having a minimum viscosity of 3 and a maximum viscosity of 3.8 cps in a 0.1% aqueous solution and a particle size such that retention on a 20 mesh sieve is 2%, on a 30 mesh sieve is 20%, and 30% passes through a 100 mesh sieve. A commercial high molecular weight polyacrylamide polymer (substantially pure polyacrylamide is about 1% hydrolyzed) has a molecular weight of 5 million. Polyacrylamide derivative in the context of the present invention is hydrolyzed in the range of about 10-35%.

The effect of these polymers on the dentin abrasive properties of a dentifrice composition is shown in Table I using a composition containing 25% glycerine, 20% silica abrasive, 1% sodium lauryl sulfate, 0.5% sodium benzoate, 52.5% water and 1% of the test polymers. Dentin abrasivity is measured by a radioactive tracer method recommended by the American Dental Association.

It could be desirable to reduce the abrasivity while retaining or improving stain removal is measured by an in vitro test. Sections of human dental enamel are etched with 0.1N HCl for 2 minutes, rinsed with water, then wet with a dilute solution of stannous fluoride, wiped dry, and finally exposed to a stream of hydrogen sulfide gas which results in the deposition of a brown deposit of stannous sulfide. The amount of stain on the surface is measured with a Gardner Automatic Color Difference meter. The surface is then brushed with a mechanical brushing machine for 500 reciprocal strokes with a slurry of a dentifrice and the residual stain measured with the meter. Finally, the stain which remains is completely removed with dental pumice and the reflectance of this surface is read. The ability of a dentifrice to remove the stain is expressed by the following equation.

$$\text{Percent stain removed} = \frac{(Rd_{500 \text{ strokes}} - Rd_{\text{initial}}) \, 100}{Rd_{\text{pumiced}} - Rd_{\text{initial}}}$$

where $Rd_{\text{initial}}$, $Rd_{500 \text{ strokes}}$, and $Rd_{\text{pumices}}$ are respectively the reflectance values measured on the initially stained surfaces, after brushing for 500 reciprocal strokes and after removing the residual stain by pumicing.

TABLE I

| Polymer | M.W. | RDA | % Stain Removal |
|---|---|---|---|
| CMC[1] (control) | — | 71 | 44 |

TABLE I-continued·

| Polymer | M.W. | RDA | % Stain Removal |
|---|---|---|---|
| PEO[2] | $4 \times 10^6$ | 59 | 64 |
| PEO[2] | $2 \times 10^6$ | 51 | 64 |
| PEO[2] | $1 \times 10^6$ | 63 | 54 |
| PAM[3] (35% hydrolyzed) | $4 \times 10^6$ | 40 | 57 |
| PAM | $5 \times 10^6$ | 66 | 48 |

[1]Carboxymethylcellulose (control)
[2]Polyethyleneoxide polymers, Polyox products available from Union Carbide
[3]Polyacrylamide polymer The results show that the 35% hydrolyzed polyacrylamide polymer derivative is more effective than the polyethylene oxide polymers in reducing dentin abrasivity and is substantially as effective for stain removal. It is also noted that the 35% hydrolyzed polyacrylamide polymer derivative is more effective than the pure polyacrylamide polymer and the control in reducing dentin abrasivity and increasing stain removal.

The guar gum polymer is a carbohydrate polymer containing galactose and mannose, in the ratio of one galactose unit for every two mannose units. It is composed primarily of high molecular weight hydrocolloidal polysaccharide, galactose and mannose units combined through glycosidic linkages and may be described chemically as a galactomannan. Derivatives of guar gum include carboxymethyl (anionic), and hydroxyalkyl (nonionic) guar gum derivatives; and a double derivative of guar gum, hydroxypropylated and carboxymethylated (anionic) guar gum which is the preferred guar gum derivative used in present inventioon. Jaguar CMHP, a commercial product available from Celanese is a double derivative of guar gum in the form of a powder having a particle size such that a minimum of 95% passes through 150 mesh. The anionic polymer has been hydroxyproplated and carboxymethylated. This product has excellent thickening and suspending properties plus superior electrolyte compatibility and low pH stability. It has a viscosity of 4,000±200 cps in a 1% aqueous solution at 25° C. using a Brookfield RVF at 20 RPM. The pH of a 1% aqueous solution is 8 to 10. The carboxymethyl hydroxypropyl guar gum holds insoluble particles in suspension better than guar gum or other commercial guar gum derivatives.

The effect of guar gum derivatives on the dentin abrasive properties of a dentifrice composition is shown in Table II using the same composition as in Table I.

TABLE II

| Polymer | RDA | % Stain Removal |
|---|---|---|
| CMC(control) | 61 | 40 |
| Jaguar HP-60[1] | 62 | 35 |
| Jaguar HP-8[2] | 52 | 34 |
| Jaguar CMHP[3] | 44 | 33 |

[1]Hydroxypropyl guar gum supplied by Celanese Cop.
[2]Hydroxypropyl guar gum (Celanese)
[3]Carboxymethyl hydroxypropyl guar gum (Celanese)

The results show that the carboxymethyl-hydroxypropyl guar gum is more effective than the hydroxypropyl guar gum and the control in reducing dentin abrasivity and is substantially as effective for stain removal.

To make toothpastes, dental cream or dental gels, the polishing agent or agents are dispersed in a dental vehicle which contains a liquid phase comprising water and/or a humectant such as glycerine, sorbitol, xylitol, propylene glycol or polyethylene glycol 400, including suitable mixtures thereof. It is usually advantageous to use a mixture of both water and one or more humectants. Polyethylene glycols of higher molecular weight, e.g. polyethylene glycol 600 etc., may also be present. The total liquid content is generally about 20 to 80% by weight of the dentifrice (sorbitol, generally present in admixture with water, is considered as a liquid for this purpose). The preferred humectants are glycerine, sorbitol and polyethylene glycol. Typically, the vehicle contains about 20–60% by weight of humectant(s) and about 3–60% water.

The very high molecular weight water soluble linear polymers of present invention are dispersed in humectant. Water and additional humectant may then be mixed with the dispersion, and a paste, gel or cream is formed. The polishing agent, surfactant and other dental ingredients are then added.

The vehicle may also contain a thickening or gelling agent, in addition to the polyacrylamide derivative or double substituted guar gum derivative, such as the natural and synthetic gums and gum-like materials, such as Irish Moss, gum tragacanth, alkali metal (e.g.) Li, K or Na) carboxymethyl cellulose and hydroxymethyl carboxymethyl cellulose, polyvinylpyrrolidone, starch, xylitol, water soluble hydrophilic colloidal carboxyvinyl polymers such as those sold under the trademark Carbopol 934 and 940, hydroxyethyl cellulose, Indian gum, acacia gums, agar, locust bean gum, Laponite CP or SP, which are each synthetic inorganic complex silicate clays sold under trademark Laponite by Laporte Industries, Ltd., and pectin or inorganic thickeners such as colloidal silica, e.g. synthetic finely divided silica including those sold under the trademarks Cab-O-Sil M5, Syloid 244, Syloid 266, Zeosyl 200 and Aerosil D200. The solid portion of the vehicle is typically present in an amount up to about 10% by weight of the toothpaste and preferably within the range of about 0.5–8% by weight.

The toothpaste may also contain surface-active agents, e.g., to achieve increased prophylactic action, assist in achieving thorough and complete dispersion of the instant compositions throughout the oral cavity, and render the instant compositions more cosmetically acceptable. The organic surface-active material may be anionic, nonionic, ampholytic, or cationic in nature, and it is preferred to employ as the surface active agent a detersive material which imparts to the composition detersive and foaming properties. Suitable types of such detergents are water soluble salts of higher fatty acid monoglyceride monosulfates, such as sodium salt of the monosulfated monoglyceride or hydrogenated coconut oil fatty acids, higher alkyl sulfates, such as sodium lauryl sulfate, alkyl aryl sulfonates, such as sodium dodecyl benzene sulfonate, higher alkyl sulfoacetates, higher fatty acid ester of 1,2-hydroxypropane sulfonates, and the substantially saturated higher aliphatic acyl amides of lower aliphatic amino carboxylic acid compounds, such as those having 12 to 16 carbons in the fatty acid alkyl or acyl radicals, and the like. Examples of the last-mentioned amides are N-lauroyl sarcosine and the sodium, potassium, and ethanolamine salts of N-lauroyl, N-myristoyl or N-palmitoyl sarcosinates, which should be substantially free from soap or similar higher fatty acid material which tends to substantially reduce the effect of these compounds. The use of these sarcosinate compounds in dentifrice compositions of the present invention is particularly advantageous since these materials exhibit a prolonged and marked effect in the inhibition of acid in the oral cavity due to carbohydrates, in addition to exerting some reduction in the solubility of tooth enamel in acid solutions.

Other suitable surface active materials include nonionic agents such as condensates of sorbitan monostearate with approximately 60 moles of ethylene oxide, condensate of ethylene oxide with propylene oxide condensates of propylene glycol ("Pluronics"), and cationic surface active germicides and antibacterial compounds such as di-isobutylphenoxyethyldimethyl benzyl ammonium chloride, benzyl dimethyl stearyl ammonium chloride, tertiary amines having one fatty alkyl group (of from 12 to 18 carbon atoms) and two (poly) oxyethylene groups attached to the nitrogen (typically containing a total of from about 2 to 50 ethenoxy groups per mole) and salts thereof with acids, and compounds of the structure:

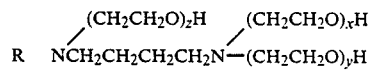

where R is a fatty alkyl group containing from about 12 to 18 carbon atoms, and x, y and z total 3 or higher, as well as salts thereof with mineral organic acids, may also be used. It is preferred that the total amount of surface-active agent be about 0.05–5% by weight, preferably about 1–3%, of the dentifrice.

The compositions of the present invention, may also contain a fluoride-containing compound having a beneficial effect on the care and hygiene of the oral cavity, e.g. diminution of enamel solubility in acid and protection of the teeth against decay. Examples thereof include sodium fluoride, stannous fluoride, potassium fluoride, potassium stannous fluoride ($SnF_2$—KF), potassium fluorozirconate, sodium hexafluorostannate, stannous chlorfluoride, and sodium monofluorophosphate. These materials, which dissociate or release fluorine-containing ions, suitably may be present in an effective but non-toxic amount, usually within the range of about 0.1 to 1% by weight, based on the water soluble fluorine content thereof. Sodium fluoride, stannous fluoride and sodium monofluorophosphate are particularly preferred, as well as mixtures thereof.

Various other materials may be incorporated in the oral preparation of this invention. Examples thereof are coloring or whitening agents such as titanium dioxide, preservatives such as sodium benzoate, silicones, chlorophyll compounds, ammoniated materials such as urea, diammoniumphosphate and mixture thereof, flavors, and other constituents. Each of these adjuvants may be typically incorporated in the instant toothpastes in amounts up to 5% provided they do not adversely affect the abrasivity and cleaning properties of the dentifrice.

The dentifrices should have a pH practicable for use, e.g. about 4–10, and preferably about 6–9.

The following examples are given to illustrate this invention further, but it is understood that the invention is not limited thereto. Dentifrice formulations are prepared in the usual manner except as indicated, and all amounts and proportions are by weight except as otherwise indicated.

EXAMPLES 1-3

| Ingredients | 1 Dental Cream % | 2 Dental Cream % | 3 Dentifrice Gel % |
|---|---|---|---|
| Silica | 24.00 | 24.00 | 18.00 |
| Calcined Alumina | 10.00 | 10.00 | — |
| Sodium Benzoate | 0.50 | 0.50 | 0.50 |
| Sodium Saccharin | 0.20 | 0.20 | 0.30 |
| Sodium Monofluorofluorophosphate | 0.76 | 0.76 | 0.76 |
| Titanium Dioxide | 0.40 | 0.40 | 0.01 |
| Flavor | 1.10 | 1.10 | 0.69 |
| Sodium Lauryl Sulfate | 1.20 | 1.20 | 1.20 |
| Water | 35.44 | 35.84 | 3.00 |
| Glycerine | 25.00 | 25.00 | 25.00 |
| Sorbitol (70% solution) | — | — | 40.84 |
| Silica Thickener | — | — | 5.50 |
| Polyethylene Glycol | — | — | 3.00 |
| Color | — | — | 0.20 |
| Carboxymethyl cellulose (CMC) | 0.40 | — | — |
| PAM (35% hydrolyzed) (m.w. about 4 × 10⁶) | 1.00 | 1.00 | 1.00 |
| RDA Value | 86 | 71 | 35 |
| % Stain Removal | 75 | 75 | 44 |

Omitting the 1% polyacrylamide (35% hydrolyzed) polymer from Example 2 and replacing it with 1.4% CMC while reducing water by 0.4% gives an RDA value of 110 and a stain removal of 75%.

Omitting the 1% polyacrylamide (35% hydrolyzed) polymer from Example 3 and replacing it with 0.35% CMC and 0.65% additional sorbitol (70%) gives an RDA value of 65 and a stain removal of 35%.

The addition of 1% of the high molecular weight water soluble linear poly-acrylamide polymer derivative to dentifrice compositions containing polishing agents such as calcined alumina and/or silica causes significant reductions in dentifrice abrasivity (Examples 1-3) and can increase the stain removal properties of the dentifrice gel (Example 3).

EXAMPLE 4-7

| Ingredients | Ex.4 % | Ex. 5 % | Ex. 6 % | Ex. 7 % |
|---|---|---|---|---|
| Sodium Carboxymethyl cellulose | 1.00 | — | — | — |
| PEO (m.w. 2 × 10⁶) | — | 1.00 | — | — |
| PAM 35% hydrolyzed m.w. = about 4 × 10⁶ | — | — | 1.00 | — |
| PAM m.w. = 5 × 10⁶ | — | — | — | 1.00 |
| Silica | 20 | 20 | 20 | 20 |
| Glycerine | 25 | 25 | 25 | 25 |
| Water | 52.5 | 52.5 | 52.5 | 52.5 |
| Sodium lauryl sulfate | 1.0 | 1.0 | 1.0 | 1.0 |
| Sodium benzoate | 0.5 | 0.5 | 0.5 | 0.5 |
| RDA | 71 | 51 | 40 | 66 |
| % Stain Removal | 44 | 66 | 57 | 48 |

Example 6 containing the 35% hydrolyzed polyacrylamide polymer exhibits the greatest reduction in dentin abrasivity and improved stain removal properties.

EXAMPLES 8-10

| Ingredients | 8 Dental Cream % | 9 Dental Cream % | 10 Dentifrice Gel % |
|---|---|---|---|
| Silica | 24.00 | 24.00 | 18.00 |
| Calcined Alumina | 10.00 | 10.00 | — |
| Sodium Benzoate | 0.50 | 0.50 | 0.50 |
| Sodium Saccharin | 0.20 | 0.20 | 0.30 |
| Sodium Monofluorophosphate | 0.76 | 0.76 | 0.76 |
| Titanium dioxide | 0.40 | 0.40 | 0.01 |
| Flavor | 1.10 | 1.10 | 0.69 |
| Sodium Lauryl Sulfate | 1.20 | 1.20 | 1.20 |
| Water | 35.44 | 35.84 | 3.00 |
| Glycerine | 25.00 | 25.00 | 25.00 |
| Sorbitol (70% solution) | — | — | 40.84 |
| Silica Thickener | — | — | 5.50 |
| Polyethylene Glycol | — | — | 3.00 |
| Color | — | — | 0.20 |
| Carboxymethyl cellulose | 0.40 | — | — |
| Carboxymethyl Hydroxypropyl Guar Gum (mw about 4 × 10⁶) | 1.00 | 1.00 | 1.00 |

It is also within the scope of the invention to include polishing agents in the dentifrice compositions other than the silica in the Examples, such as hydrated alumina, dicalcium phosphate dihydrate, calcium carbonate, or calcium pyrophosphate, etc.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

I claim:

1. A dentifrice composition having reduced dentin abrasivity and improved cleaning properties comprising an abrasive system consisting of at least 15% by weight of one or more dentally acceptable polishing agents and an effective amount of about 0.1-2.0% by weight of a water soluble high molecular weight above one million linear polymer selected from the group consisting of 10-35% hydrolyzed polyacrylaminde and anionic, nonionic, double substituted guar gum to reduce the dentin abrasion of the dentifrice, in a dental vehicle.

2. A composition according to claim 1, wherein the polymer is 10-35% hydrolyzed polyacrylamide.

3. The composition according to claim 1, wherein the polymer is hydroxypropylated carboxymethylated guar gum.

4. The composition according to claim 1, wherein the abrasive system consists of a siliceous polishing agent.

5. The composition according to claim 1 wherein the abrasive system is a combination of a siliceous polishing agent and calcined alumina.

6. The composition according to claim 1, wherein the abrasive system constitutes about 15-75% by weight of the dentifrice.

7. The composition according to claim 2, wherein the polyacrylamide is a 35% partially hydrolyzed polyacrylamide and is present in an amount of about 1–2% by weight of the composition.

8. The composition according to claim 5, wherein the siliceous polishing agent constitutes about 20–50% by weight, and the calcined alumina constitutes about 5 to 15% by weight of the dentifrice.

9. The composition according to claim 1, wherein the dental vehicle contains about 20–80% by weight of a liquid phase comprising water and humectant.

10. The composition according to claim 9, wherein the humectant content constitutes about 20–60% by weight, and the water constitutes about 3–60% by weight of the composition.

11. The composition according to claim 10, additionally containing an anionic surfactant.

12. The composition according to claim 10, wherein the humectant content constitutes 40% by weight of a mixture of glycerine, sorbitol and polyethylene glycol, and the water content constitutes about 15% by weight.

13. The composition according to claim 10, wherein the humectant constitutes 25% glycerine and the water constitutes 36% by weight.

14. The composition according to claim 3, wherein hydroxypropylated carboxymethylated guar gum constitutes about 1% by weight of the composition.

* * * * *